United States Patent [19]

Beigelman et al.

[11] Patent Number: 5,840,876
[45] Date of Patent: Nov. 24, 1998

[54] 2'-O-ALKYLTHIOALKYL AND 2'-C-ALKYLTHIOALKYL-CONTAINING NUCLEIC ACIDS

[75] Inventors: Leonid Beigelman, Longmont; Alex Karpeisky, Boulder, both of Colo.

[73] Assignee: Ribozyme Pharmaceuticals, Inc., Boulder, Colo.

[21] Appl. No.: 873,793

[22] Filed: Jun. 12, 1997

Related U.S. Application Data

[63] Continuation of Ser. No. 426,124, Apr. 20, 1995, Pat. No. 5,716,824.

[51] Int. Cl.$^6$ .......................... C07H 21/04; C07H 21/00; C12Q 1/68; A61K 48/00
[52] U.S. Cl. .......................... 536/25.3; 435/6; 435/91.31; 435/179; 435/366; 536/23.1; 536/24.3; 536/25.1; 514/44
[58] Field of Search .................................. 435/5, 6, 91.1, 435/91.31, 172.1, 179, 325, 366, 172.3; 536/23.1, 24.5, 24.3, 25.3, 24.1, 25.1, 23.2; 514/44

[56] References Cited

U.S. PATENT DOCUMENTS

| | | | |
|---|---|---|---|
| 4,987,071 | 1/1991 | Cech et al. . | |
| 5,264,562 | 11/1993 | Matteucci | 536/23.1 |
| 5,334,711 | 8/1994 | Sproat et al. . | |
| 5,434,257 | 7/1995 | Matteucci et al. | 536/24.3 |
| 5,495,009 | 2/1996 | Matteucci et al. | 536/25.3 |
| 5,627,053 | 5/1997 | Usman et al. | 435/91.1 |
| 5,639,647 | 6/1997 | Usman et al. | 435/199 |
| 5,672,501 | 9/1997 | Matulic-Acamic et al. | 435/240.2 |
| 5,672,511 | 9/1997 | Beigelman et al. | 435/325 |

FOREIGN PATENT DOCUMENTS

| | | |
|---|---|---|
| 0360257 | 3/1990 | European Pat. Off. . |
| 9106629 | 5/1991 | WIPO . |
| 9207065 | 4/1992 | WIPO . |
| 93415187 | 5/1993 | WIPO . |
| 9402595 | 3/1994 | WIPO . |
| 9506764 | 3/1995 | WIPO . |
| 9531470 | 11/1995 | WIPO . |

OTHER PUBLICATIONS

Cech, "Ribozymes and Their Medical Implications," *JAMA* 260:3030–3034 (1988).
Collins and Olive, "Reaction Conditions and Kenetics of Self–Cleavage of a Ribozyme Derived From Neurospora VS RNA," *Biochemistry* 32:2795–2799 (1993).
Egholm et al., "PNA hybridizes to complementary oligonucleotides obeying the Watson–Crick hydrogen–bonding rules," *Nature* 365:566–568 (1993).
Guerrier–Takada et al., "The RNA Moiety of Ribonuclease P Is the Catalytic Subunit of the Enzyme," *Cell* 35:849–857 (1983).
Hampel et al., "'Hairpin' Catalytic RNA Model: Evidence for Helices and Sequence Requirement for Substrate RNA," *Nucleic Acids Research* 18:299–304 (1990).
Hampel and Tritz, "RNA Catalytic Properties of the Minimum (–)s TRSV Sequence," *Biochemistry* 28:4929–4933 (1989).
Haseloff and Gerlach, "Simple RNA Enzymes with New and Highly Specific Endoribonuclease Activities," *Nature* 334:585–591 (1988).
Heidenreich et al., "High activity and stability of hammerhead ribozymes containing 2'modified pyrimidine nucleosides and phosphorothioates," *J. Biol. Chem.* 269(3):2131–2138 (1994).
Jeffries and Symons, "A Catalytic 13–mer Ribozyme," *Nucleic Acids Research* 17:1371–1377 (1989).
Jones et al., "Synthesis and Binding Properties of Pyrimidine Oligodeoxynucleoside Analogs Containing Neutral Phosphodiester Replacements: The Formacetal and 3'–Thioformacetal Internucleoside Linkages," *J. Org. Chem.* 58:2983–2991 (1993).
Kim and Cech, "Three–dimensional model of the active site of the self–splicing rRNA precursor of the Tetrahymena," *Proc. Natl. Acad. Sci. USA* 84:8788 (1987).
Mattecci et al., "Deoxyoligonucleotide Analogs Based on Formacetal Linkages," *Tetrahedron Lett.* 31:2385–2388 (1990).
Medina et al., "A Mild Method for the Conversion of Alcohols to Methylthiomethyl Ethers," *Tetrahedron Lett.* 29:3773–3776 (1988).
Perreault et al., "Mixed Deoxyribo– and Ribo–Oligonucleotides with Catalytic Activity," *Nature* 344:565–567 (1990).
Perrotta and Been, "Cleavage of Oligoribonucleotides by a Ribozyme Derived from the Hepatitis δ Virus RNA Sequence," *Biochemistry* 31:16–21 (1992).
Pieken et al., "Kinetic Characterization of Ribonuclease–Resistant 2'–Modified Hammerhead Ribozymes," *Science* 253:314–317 (1991).

(List continued on next page.)

*Primary Examiner*—W. Gary Jones
*Assistant Examiner*—Jeffrey Fredman
*Attorney, Agent, or Firm*—Lyon & Lyon LLP

[57] ABSTRACT

A compound having the formula:

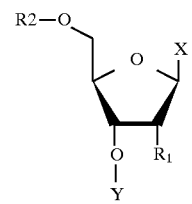

wherein, R1 represents 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester; X represents a base or H; Y represents a phosphorus-containing group; and R2 represents H, DMT or a phosphorus-containing group.

6 Claims, 8 Drawing Sheets

OTHER PUBLICATIONS

Pudlo et al., "Deoxyoligonucleotides containing 2'5' acetal linkages; synthesis and hybridization properties," *Tetrahedron Letters* 35(50):9315–9318 (1994).

Quaedflieg et al., "An Alternative Route to the Preparation of (3'→5') Methyelne Acetal Linked Di– and Trinucleosides," *Synthesis* pp. 627–633 (Jun. 1993).

Saville and Collins, "A Site–Specific Self–Cleavage Reaction Performed by a Novel RNA In Neurospora Mitochondria," *Cell* 61:685–696 (1990).

Saville and Collins, "RNA–Medicated Ligation of Self––Cleavage Products of a Neurospora Mitochondrial Plasmid Transcript," *Proc. Natl. Acad. Sci. USA* 88:8826–8830 (1991).

Scaringe et al."Chemical synthesis of biologically active oligoribonucleotides using β–cynaoethyl protected ribonucleoside phosphoramidites," *Nucl Acids Res.* 18:5433–5441 (1990).

Stein and Cheng, "Antisense Oligonucleotides as Therpeutic Agents—Is the Bullet Really Really Magical?," *Science* 261:1004–1012 (1993).

Torrence et al., "Targeting RNA for degredation with a (2'–5')oligoadenylate–antisense chimera," *Proc. Natl. Acad. Sci. USA* 90:1300–1304 (1993).

Uhlenbeck, "A Small Catalytic Oligoribonucleotide," *Nature* 328:596–600 (1987).

Usman and Cedrgren, "Exploiting the chemical synthesis of RNA," *TIBS* 17:334–339 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Symposium Series* 31:163–164 (1994).

Veeneman et al., "Synthesis of Oligodeoxynucleotides Containing Thymidines Linked Via An Internucleosidic–(3' 5')–Methylene Bond," *Recl. Trav. Chim. Pays–Bas*109:449–451 (1990).

Zavgorodny et al., "1–Alkylthioalkylation of Nucleoside Hydroxyl Functions and Its Synthetic Application: A New Versatile Method in Nucleoside Chemistry," *Tetrahedron Lett.* 32:7593–7596 (1991).

HAMMERHEAD RIBOZYME SUBSTRATE MOTIFS

Fig. 4 HEPATITIS DELTA VIRUS RIBOZYME

HAMMERHEAD RIBOZYMES TARGETED AGAINST STROMELYSIN RNA
Fig. 7

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.
            The letter "H"stands for C, A or U.

( x i ) SEQUENCE DESCRIPTION: SEQ ID NO: 1:

NNNNUHNNNN N    1 1

( 2 ) INFORMATION FOR SEQ ID NO: 2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO: 2:

NNNNCUGAN GAGNNNNNC GAAANNNN    2 8

( 2 ) INFORMATION FOR SEQ ID NO: 3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
  ( D ) OTHER INFORMATION: The letter "N" stands for any base.
    The letter "Y" is stands for U or C.
    The letter "H" stands for A, U or C.

( x i ) SEQUENCE DESCRIPTION: SEQ ID NO: 3:

NNNNNNNYNG HYNNN                                                                                  15

( 2 ) INFORMATION FOR SEQ ID NO: 4:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.

( x i ) SEQUENCE DESCRIPTION: SEQ ID NO: 4:

NNNNGAAGNN NNNNNNNNA AAHANNNNNN NACAUUACNN NNNNNNN                                                 47

( 2 ) INFORMATION FOR SEQ ID NO: 5:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 5:

UGGCCGGCAU GGUCCCAGCC UCCUCGCUGG CGCCGGCUGG GCAACAUUCC GAGGGGACCG                                  60

UCCCCUCGGU AAUGGCGAAU GGGAC                                                                       85

( 2 ) INFORMATION FOR SEQ ID NO: 6:

( i ) SEQUENCE CHARACTERISTICS:
    ( A ) LENGTH: 176 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 6:

GGGAAAGCUU GCGAAGGGCG UCGUCGCCCC GAGCGGUAGU AAGCAGGGAA CUCACCUCCA                                  60

AUUUCAGUAC UGAAAUUGUC GUAGCAGUUG ACUACUGUUA UGUGAUUGGU AGAGGCUAAG                                  120

UGACGGUAUU GGCGUAAGUC AGUAUUGCAG CACAGCACAA GCCCGCUUGC GAGAAU                                      176

( 2 ) INFORMATION FOR SEQ ID NO: 7:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 7:

AGGGAUUAAU GGAGA                                                                                  15

( 2 ) INFORMATION FOR SEQ ID NO: 8:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 8:

UCUCCAUCUG AUGAGGCCGA AAGGCCGAAA AUCCCU 36

2'-O-ALKYLTHIOALKYL AND 2'-C-ALKYLTHIOALKYL-CONTAINING NUCLEIC ACIDS

BACKGROUND OF THE INVENTION

This is a continuation of application Ser. No. 08/426,124, filed Apr. 20, 1995, now U.S. Pat. No. 5,716,824, hereby incorporated by reference herein in totality, including drawings.

This invention relates to chemically synthesized ribozymes, or enzymatic nucleic acid molecules, antisense oligonucleotides and derivatives thereof.

The following is a brief description of ribozymes and antisense nucleic acids. This summary is not meant to be complete but is provided only for understanding of the invention that follows. This summary is not an admission that all of the work described below is prior art to the claimed invention.

Ribozymes are nucleic acid molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

By the phrase enzymatic nucleic acid is meant a catalytic modified-nucleotide containing nucleic acid molecule that has complementarity in a substrate binding region to a specified gene target, and also has an enzymatic activity that specifically cleaves RNA or DNA in that target. That is, the enzymatic nucleic acid is able to intramolecularly or intermolecularly cleave RNA or DNA and thereby inactivate a target RNA or DNA molecule.

This complementarity functions to allow sufficient hybridization of the enzymatic RNA molecule to the target RNA or DNA to allow the cleavage to occur. 100% Complementarity is preferred, but complementarity as low as 50–75% may also be useful in this invention.

By "antisense nucleic acid" is meant a non-enzymatic nucleic acid molecule that binds to another RNA (target RNA) by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2-5A antisense chimera" is meant, an antisense oligonucleotide containing a 5' phosphorylated 2'-5'-linked adenylate residues. These chimeras bind to target RNA in a sequence-specific manner and activate a cellular 2-5A-dependent ribonuclease which in turn cleaves the target RNA (Torrence et al., 1993 *Proc. Natl. Acad. Sci. USA* 90, 1300).

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al, 1992, *Aids Research and Human Retroviruses* 8, 183, of hairpin motifs by Hampel et al, EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target such that specific treatment of a disease or condition can be provided with a single enzymatic nucleic acid. Such enzymatic nucleic acid molecules can be delivered exogenously to specific cells as required. In the preferred hammerhead motif the small size (less than 60 nucleotides, preferably between 30–40 nucleotides in length) of the molecule allows the cost of treatment to be reduced compared to other ribozyme motifs.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead structure) are used for exogenous delivery. The simple structure of these molecules increases the ability of the enzymatic nucleic acid to invade targeted regions of the mRNA structure. Unlike the situation when the hammerhead structure is included within longer transcripts, there are no non-enzymatic nucleic acid flanking sequences to interfere with correct folding of the enzymatic nucleic acid structure or with complementary regions.

Eckstein et al., International Publication No. WO 92/07065, Perrault et al. *Nature* 1990, 344, 565–568, Pieken, W. et al. *Science* 1991, 253, 314–317, Usman, N.; Cedergren, R. J. *Trends in Biochem. Sci.* 1992, 17, 334–339, Usman, N. et al. International Publication No. WO 93/15187 and Sproat, B. U.S. Pat. No. 5,334,711 describe various chemical modifications that can be made to the sugar moieties of enzymatic RNA molecules. All these publications are hereby incorporated by reference herein.

Medina et al., 1988 *Tetrahedron Letters* 29, 3773, describe a method to convert alcohols to methylthiomethyl ethers.

Matteucci et al., 1990 *Tetrahedron Letters*, 31, 2385, report the synthesis of 3'-5'-methylene bond via a methylthiomethyl precursor.

Veeneman et al., 1990 *Recl. Trav. Chim. Pays-Bas* 109, 449, report the synthesis of 3'-O-methylthiomethyl deoxynucleoside during the synthesis of a dimer containing 3'-5'-methylene bond.

Jones et al., 1993 *J. Org. Chem.* 58, 2983, report the use of 3'-O-methylthiomethyl deoxynucleoside to synthesize a dimer containing a 3'-thioformacetal internucleoside linkages. The paper also describes a method to synthesize phosphoramidites for DNA synthesis.

Zavgorodny et al., 1991 *Tetrahedron Letters* 32, 7593, describe a method to synthesize a nucleoside containing methylthiomethyl modification.

SUMMARY OF THE INVENTION

This invention relates to the incorporation of 2'-O-$R_3$-thio-$R_3$ and/or 2'-C-$R_3$-thio-$R_3$, wherein $R_3$ is independently a compound selected from a group consisting of alkyl, alkenyl, alkynyl, aryl, alkylaryl, carbocyclic aryl, heterocyclic aryl, amide and ester nucleotides or non-nucleotides into nucleic acids, which are particularly useful for enzymatic cleavage of RNA or single-stranded DNA, and also as antisense oligonucleotides.

As the term is used in this application, 2'-O-$R_3$-thio-$R_3$ and/or 2'-C-$R_3$-thio-$R_3$, wherein $R_3$ is independently a compound selected from a group consisting of alkyl, alkenyl, alkynyl, aryl, alkylaryl, carbocyclic aryl, heterocyclic aryl, amide and ester nucleotide or non-nucleotide-containing enzymatic nucleic acids are catalytic nucleic molecules that contain 2'-O-$R_3$-thio-$R_3$ and/or 2'-C-$R_3$-thio-$R_3$, wherein $R_3$ is independently a compound selected from a group consisting of alkyl, alkenyl, alkynyl, aryl, alkylaryl, carbocyclic aryl, heterocyclic aryl, amide and ester nucleotide or non-nucleotides components replacing one or more bases or regions including, but not limited to, those bases in double stranded stems, single stranded "catalytic core" sequences, single-stranded loops or single-stranded recognition sequences. These molecules are able to cleave (preferably, repeatedly cleave) separate RNA or DNA molecules in a nucleotide base sequence specific manner. Such catalytic nucleic acids can also act to cleave intramolecularly if that is desired. Such enzymatic molecules can be targeted to virtually any RNA transcript.

Also within the invention are 2'-O-$R_3$-thio-$R_3$ and/or 2'-C-$R_3$-thio-$R_3$, wherein $R_3$ is independently a compound selected from a group consisting of alkyl, alkenyl, alkynyl, aryl, alkylaryl, carbocyclic aryl, heterocyclic aryl, amide and ester nucleotides or non-nucleotides which may be present in enzymatic nucleic acid or in antisense oligonucleotides or 2-5A antisense chimera. Such nucleotides or non-nucleotides are useful since they enhance the activity of the antisense or enzymatic molecule. The Invention also relates to novel intermediates useful in the synthesis of such nucleotides or non-nucleotides and oligonucleotides (examples of which are shown in the Figures), and to methods for their synthesis.

Thus, in a first aspect, the invention features 2'-O-$R_3$-thio-$R_3$ wherein $R_3$ is independently a compound selected from a group consisting of alkyl, alkenyl, alkynyl, aryl, alkylaryl, carbocyclic aryl, heterocyclic aryl, amide and ester nucleosides or non-nucleosides, that is a nucleoside or non-nucleosides having at the 2'-position on the sugar molecule a 2'-O-$R_3$-thio-$R_3$ wherein $R_3$ is independently a compound selected from a group consisting of alkyl, alkenyl, alkynyl, aryl, alkylaryl, carbocyclic aryl, heterocyclic aryl, amide and ester moiety. In a related aspect, the invention also features 2'-O-$R_3$-thio-$R_3$, wherein $R_3$ is independently a compound selected from a group consisting of alkyl, alkenyl, alkynyl, aryl, alkylaryl, carbocyclic aryl, heterocyclic aryl, amide and ester nucleotides or non-nucleotides. That is, the invention preferably includes those nucleotides or non-nucleotides having 2' substitutions as noted above useful for making enzymatic nucleic acids or antisense molecules that are not described by the art discussed above.

The term non-nucleotide refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenine, guanine, cytosine, uracil or thymine. It may have substitutions for a 2' or 3' H or OH as described in the art. See Eckstein et al. and Usman et al., supra.

The term nucleotide refers to the regular nucleotides (A, U, G, T and C) and modified nucleotides such as 6-methyl U, inosine, 5-methyl C and others. Specifically, the term U, "nucleotide" is used as recognized in the art to include natural bases, and modified bases well known in the art. Such bases are generally located at the 1' position of a sugar moiety. The term "non-nucleotide" as used herein to encompass sugar moieties lacking a base or having other chemical groups in place of a base at the 1' position. Such molecules generally include those having the general formula:

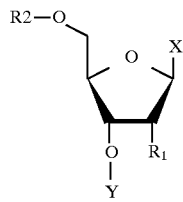

wherein, R1 represents 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester; X represents a base or H; Y represents a phosphorus-containing group; and R2 represents H, DMT or a phosphorus-containing group.

Phosphorus-containing group is generally a phosphate, thiophosphate, H-phosphonate, methylphosphonate, phosphoramidite or other modified group known in the art.

In a second aspect, the invention features 2'-C-R$_3$-thio-R$_3$ wherein R$_3$ is independently a compound selected from a group consisting of alkyl, alkenyl, alkynyl, aryl, alkylaryl, carbocyclic aryl, heterocyclic aryl, amide and ester nucleosides or non-nucleosides, that is a nucleotide or a non-nucleotide residue having at the 2'-position on the sugar molecule a 2'-C-R$_3$-thio-R$_3$ wherein R$_3$ is independently a compound selected from a group consisting of alkyl, alkenyl, alkynyl, aryl, alkylaryl, carbocyclic aryl, heterocyclic aryl, amide and ester moiety. In a related aspect, the invention also features 2'-C-R$_3$-thio-R$_3$ wherein R$_3$ is independently a compound selected from a group consisting of alkyl, alkenyl, alkynyl, aryl, alkylaryl, carbocyclic aryl, heterocyclic aryl, amide and ester nucleotides or non-nucleotides. That is, the invention preferably includes all those 2' modified nucleotides or non-nucleotides useful for making enzymatic nucleic acids or antisense molecules as described above that are not described by the art discussed above.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, =O, =S, NO$_2$ or N(CH$_3$)$_2$, amino, or SH. The term alkenyl refers to unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, =O, =S, NO$_2$, halogen, N(CH$_3$)$_2$, amino, or SH. The term alkynyl refers to groups which have an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, NO$_2$ or N(CH$_3$)$_2$, amino or SH.

An "aryl" group refers to an aromatic group which has at least one ring having a conjugated π electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above. Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

In other aspects, also related to those discussed above, the invention features oligonucleotides having one or more 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester nucleotides or non-nucleotides; e.g. enzymatic nucleic acids having a 2'-C-R$_3$-thio-R$_3$ wherein R$_3$ is independently a compound selected from a group consisting of alkyl, alkenyl, alkynyl, aryl, alkylaryl, carbocyclic aryl, heterocyclic aryl, amide and ester nucleotides or non-nucleotides; and a method for producing an enzymatic nucleic acid molecule having enhanced activity to cleave an RNA or single-stranded DNA molecule, by forming the enzymatic molecule with at least one nucleotide or a non-nucleotide moiety having at its 2'-position an 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester group.

In other related aspects, the invention features 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester nucleotide triphosphates. These triphosphates can be used in standard protocols to form useful oligonucleotides of this invention.

The 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester derivatives of this invention provide enhanced activity and stability to the oligonulceotides containing them.

In yet another preferred embodiment, the invention features oligonucleotides having one or more 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester abasic (non-nucleotide) moeities. For example, enzymatic nucleic acids having a 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester abasic moeity; and a method for producing an enzymatic nucleic acid molecule having enhanced activity to cleave an RNA or single-stranded DNA molecule, by forming the enzymatic molecule with at least one position having at its 2'-position an 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester group.

In related embodiments, the invention features enzymatic nucleic acids containing one or more 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester substitutions either in the enzymatic portion, substrate binding portion or both, as long as the catalytic activity of the ribozyme is not significantly decreased.

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–3 as discussed below. That is, these arms contain sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 1).

In yet another preferred embodiment, the invention features the use of 2'-O-alkylthioalkyl moieties as protecting groups for 2'-hydroxyl positions of ribofuranose during nucleic acid synthesis.

Other features and advantages of the invention will be apparent from the following description of the preferred embodiments thereof, and from the claims.

DESCRIPTION OF THE PREFERRED EMBODIMENTS

The drawings will first briefly be described.
Drawings:

FIG. 1 (SEQ.ID.NO. 1) (SEQ.ID.NO 2) is a diagrammatic representation of the hammerhead ribozyme domain known in the art. Stem II can be ≧2 base-pair long. Each N is independently any base or non-nucleotide as used herein.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 (SEQ.ID.NO. 3) (SEQ.ID.NO. 4) is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H refers to bases A, U, or C. Y refers to pyrimidine bases. "_" refers to a covalent bond.

Figure 6:
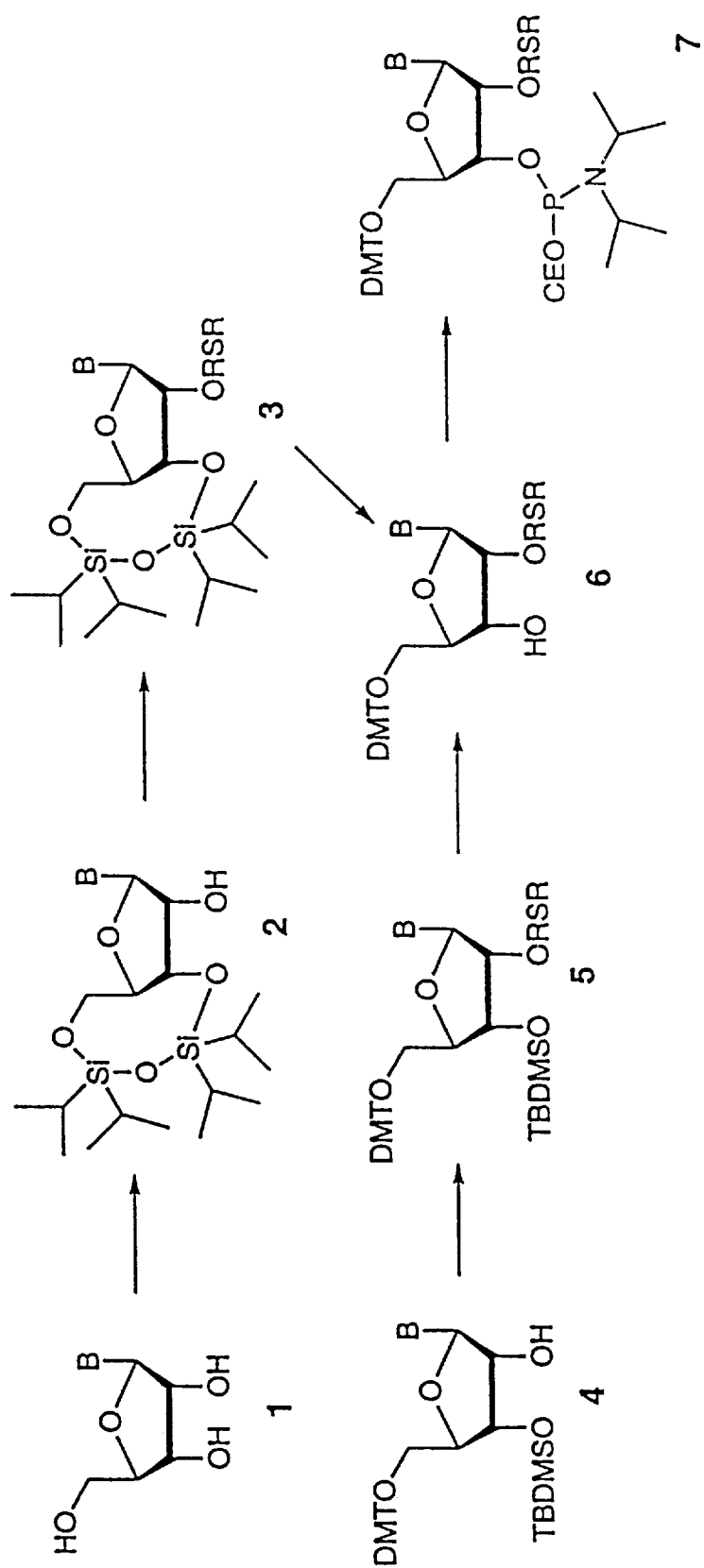

FIG. 6 is a diagrammatic representation of the synthesis of 2'-O-R$_3$-thio-R$_3$ wherein R$_3$ is independently a compound selected from a group consisting of alkyl, alkenyl, alkynyl, aryl, alkylaryl, carbocyclic aryl, heterocyclic aryl, amide and ester nucleosides or non-nucleosides and their phosphoramidites. R is an alkyl as defined above. B is any naturally occuring or modified base bearing any N-protecting group suitable for standard oligonucleotide synthesis (Usman et al., supra; Scaringe et al., supra), and/or H (non-nucleotide), as described by the publications discussed above, and those described by Usman et al., entitled "2'-deoxy-2'-alkylnucleotide containing nucleic acid" filed Mar. 29, 1994, and hereby incorporated by reference herein. CE is cyanoethyl, DMT is a standard blocking group. Other abbreviations are standard in the art.

FIG. 7 (SEQ.ID.NO. 7)(SEQ.ID.NO. 8) is a diagrammatic representation of a hammerhead ribozyme, targeted to stromelysin RNA (see Sullivan et al., WO 94/02595), containing 2'-O-methylthiomethyl substitutions.

Figure 8:
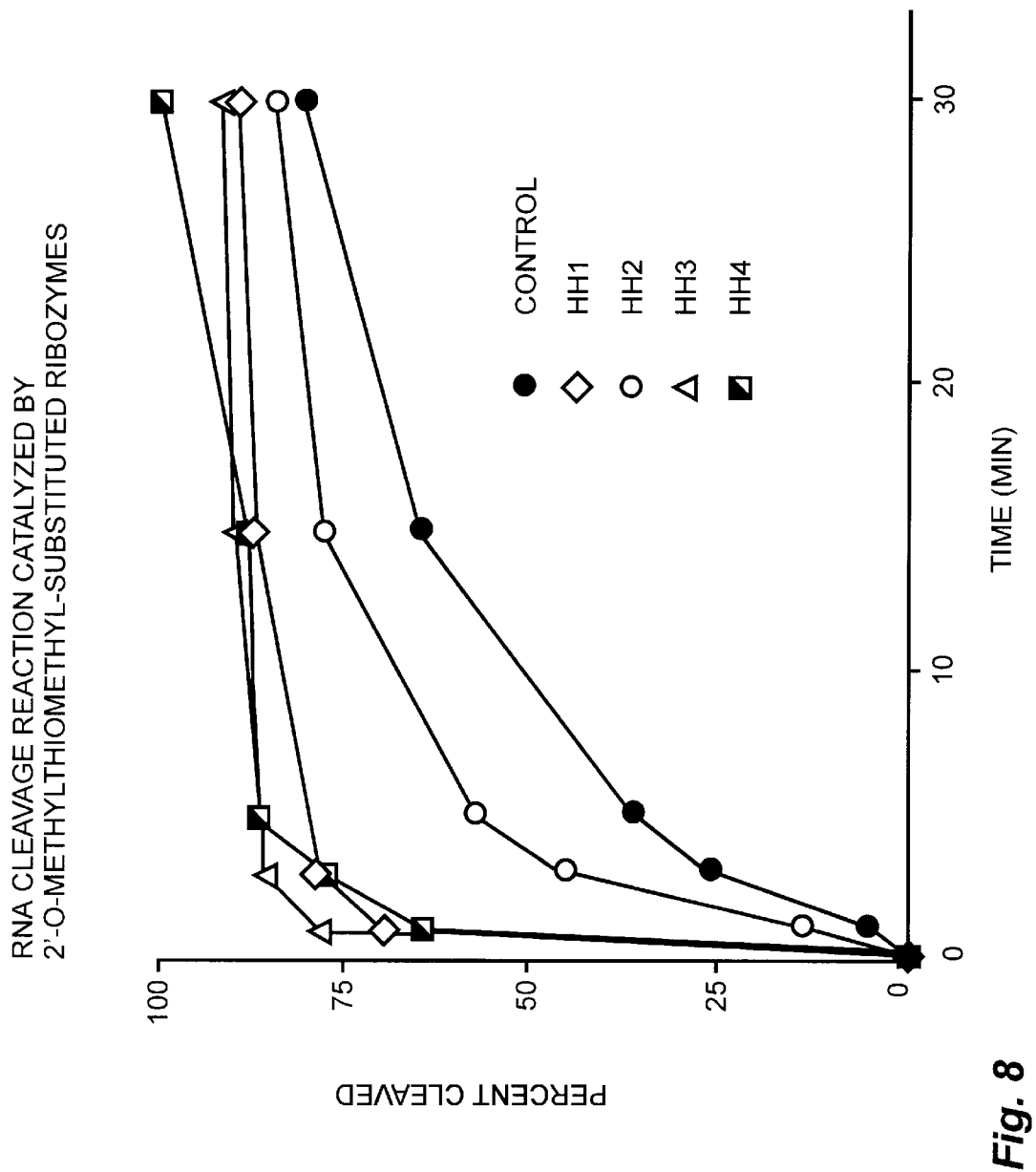

FIG. 8 shows RNA cleavage activity catalyzed by 2'-O-methylthiomethyl substituted ribozymes. A plot of percent cleaved as a function of time is shown. The reactions were carried out at 37° C. in the presence of 40 nM ribozyme, 1 nM substrate and 10 mM MgCl$_2$. Control HH ribozyme contained the following modifications; 29 positions were modified with 2'-O-methyl, U4 and U7 positions were modified with 2'-amino groups, 5 positions contained 2'-OH groups. These modifications of the control ribozyme have previously been shown not to significantly effect the activity of the ribozyme (Usman et al., 1994 *Nucleic Acids Symposium Series* 31, 163).

NUCLEOTIDES AND NUCLEOSIDES

Figure 1:
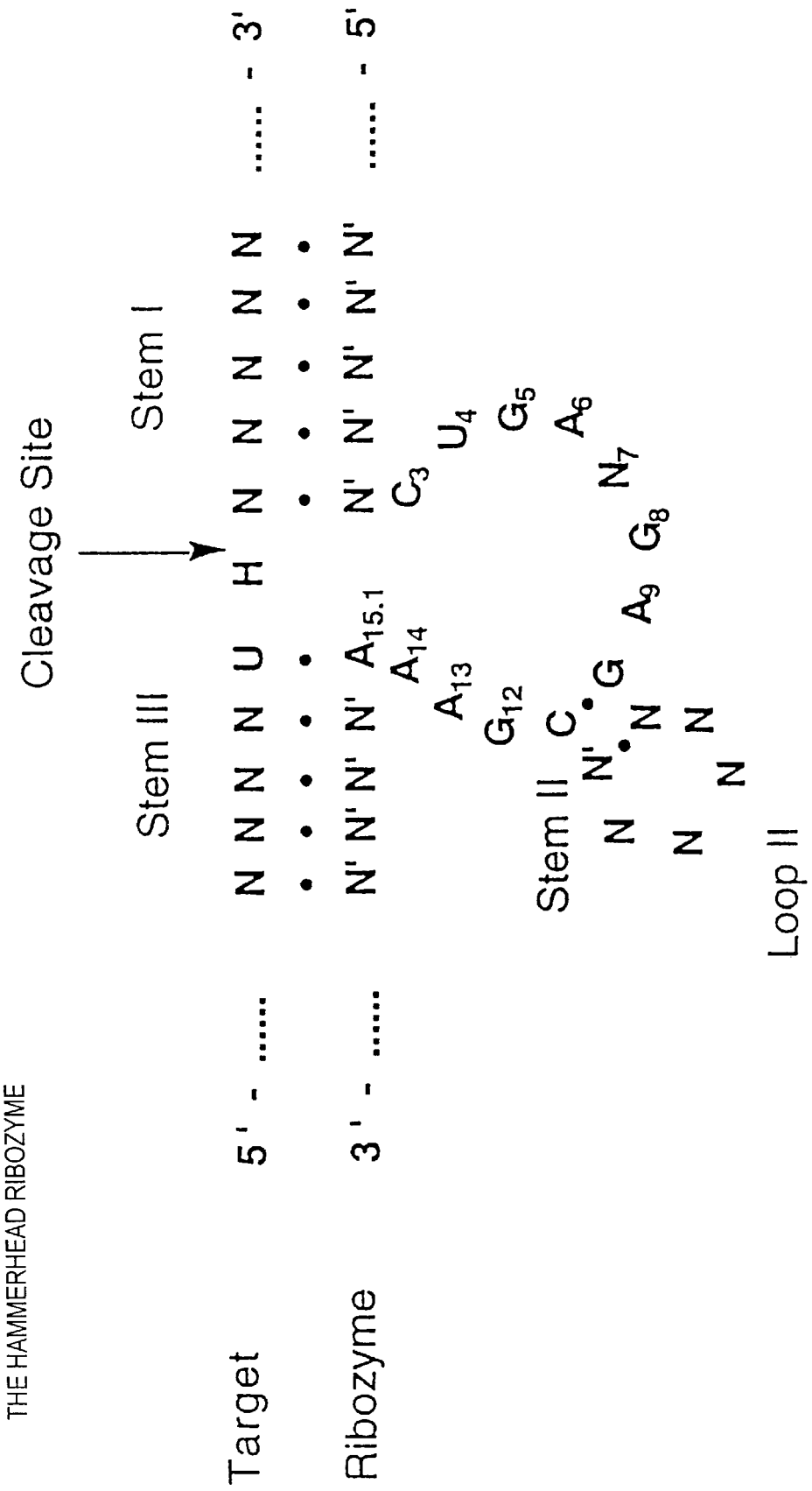
Figure 2B:
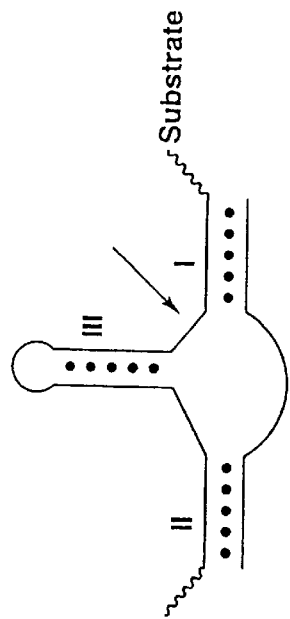
Figure 2D:
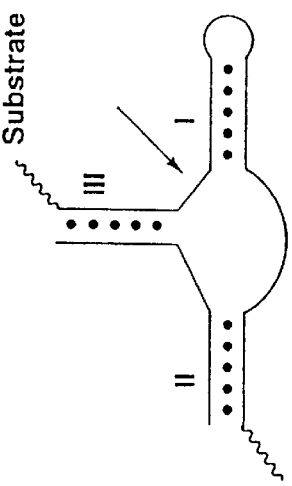
Figure 2A:
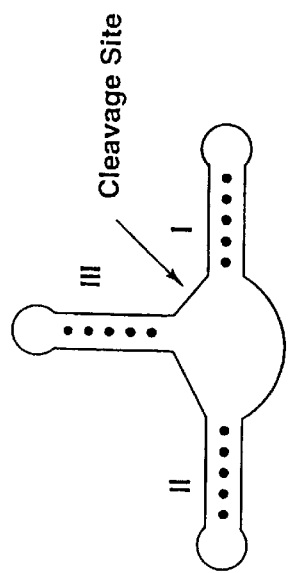
Figure 2C:
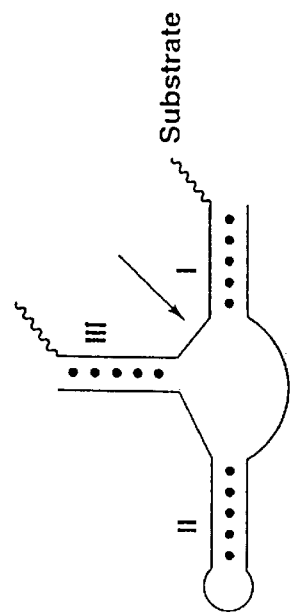

While this invention is applicable to all oligonucleotides, applicant has found that the modified molecules of this invention are particulary useful for enzymatic RNA molecules. Thus, below is provided examples of such molecules. Those in the art will recognize that equivalent procedures can be used to make other molecules without such enzymatic activity. Specifically, FIG. 1 shows base numbering of a hammerhead motif in which the numbering of various nucleotides in a hammerhead ribozyme is provided. This is not to be taken as an indication that the Figure is prior art to the pending claims, or that the art discussed is prior art to those claims.

Referring to FIG. 1, the preferred sequence of a hammerhead ribozyme in a 5'- to 3'-direction of the catalytic core is CUGANGAG [base paired with] CGAAA. In this invention, the use of 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester substituted nucleotides or non-nucleotides that maintain or enhance the catalytic activity and or nuclease resistance of the hammerhead ribozyme is described. Substitutions of any nucleotide with any of the modified nucleotides or non-nucleotides discussed above are possible. Usman et at, supra and Sproat et al., supra as well as other publications indicate those bases that can be substituted in noted ribozyme motifs. Those in the art can thus determine those bases that may be substituted as described herein with beneficial retainment of enzymatic activity and stability.

EXAMPLES

The following are non-limiting examples showing the synthesis of nucleic acids using 2'-O-methylthioalkyl-substituted phosphoramidites and the syntheses of the amidites.

Example 1: Synthesis of Hammerhead Ribozymes Containing 2'-O-alkylthioalkylnucleotides & Other Modified Nucleotides The method of synthesis follows the procedure for normal RNA synthesis as described in Usman, N.; Ogilvie, K. K.; Jiang, M.-Y.; Cedergren, R. J. *J. Am. Chem. Soc.* 1987, 109, 7845–7854 and in Scaringe, S. A.; Franklyn, C.; Usman, N. *Nucleic Acids Res.* 1990, 18, 5433–5441 and makes use of common nucleic acid protecting and coupling groups, such as dimethoxytrityl at the 5'-end, and phosphoramidites at the 3'-end. These 2'-O-R$_3$-thio-R$_3$ wherein R$_3$ is independently a compound selected from a group consisting of alkyl, alkenyl, alkynyl, aryl, alkylaryl, carbocyclic aryl, heterocyclic aryl, amide and ester substituted phosphoramidites may be incorporated not only into hammerhead ribozymes, but also into hairpin, hepatitis delta virus, Group 1 or Group 2 intron catalytic nucleic acids, or into antisense oligonucleotides. They are, therefore, of general use in any nucleic acid structure.

Example 2: Synthesis of base-protected 3,5'-O-(tetraisopropyldisiloxane-1,3-diyl) nucleosides (2)

Referring to FIG. 6, standard introduction of "Markiewicz" protecting group to the base-protected nucleosides according to "Oligonucleotides and Analogues. A Practical Approach", ed. F. Eckstein, IRL Press, 1991 resulted in protected nucleosides (2) with 85–100% yields. Briefly, in a non-limiting example, Uridine (20 g, 81.9 mmol) was dried by two coevaporations with anhydrous pyridine and re dissolved in the anhydrous pyridine. The above solution was cooled (0° C.) and solution of 1,3-dichloro-1,1,3,3-tetraisopropylsiloxane (28.82 mL, 90.09 mmol) in 30 mL of anhydrous dichloroethane was added dropwise under stirring. After the addition was completed the reaction mixture was allowed to warm to room temperature and stirred for additional two hours. Then it was quenched with MeOH (25 mL) and evaporated to dryness. The residue was dissolved in methylene chloride and washed with saturated NaHCO$_3$ and brine. The organic layer was evaporated to dryness and then coevaporated with toluene to remove traces of pyridine to give 39 g (98%) of compound 2 (B=Ura) which was used without further purification.

Other 3',5'-O-(tetraisopropyldisiloxane-1,3-di-yl)-nucleosides were obtained in 75–90% yields, using the protocol described above, starting from base-protected nucleosides with final purification of the products by flash chromatography on silica gel when necessary.

Example 3: General procedure for the synthesis of 2'-O-methylthiomethyl nucleosides (3)

Referring to FIG. 6, to a stirred ice-cooled solution of the mixture of base-protected 3',5'-O-(tetraisopropyldisiloxane-1,3-diyl) nucleoside (2) (7 mmol), methyl disulfide (70 mmol), 2,6-lutidine (7 mmol) in methylene chloride (100 mL) or mixture methylene chloride-acetonitrile (1:1) under positive pressure of argon, solution of benzoyl peroxide (28 mmol) in methylene chloride was added dropwise during 1 hour. After complete addition the reaction mixture was stirred at 0° C. under argon for additional 1 hour. The solution was allowed to warm to room temperature, diluted with methylene chloride (100 mL), washed twice with saturated aq NaHCO$_3$ and brine. The organic layer was dried over sodium sulfate and evaporated to dryness. The residue was purified by flash chromatography on silica using 1–2% methanol in methylene chloride as an eluent to give corresponding methylthiomethyl nucleosides with 55–70% yield.

Example 4: 5'-O-Dimethoxytrityl-2'O-Methylthiomethyl-Nucleosides. (6) Method A. The solution of the base-protected 3',5'-O-(tetraisopropyldisiloxane-1,3-diyl)-2'-O-methylthiomethyl nucleoside (3) (2.00 mmol) in 10 ml of dry tetrahydrofuran (THF) was treated with 1M solution of tetrabutylammoniumfluoride in THF (3.0 ml) for 10–15 minutes at room temperature. Resulting mixture was evaporated, the residue was loaded to the silica gel column, washed with 1L of chloroform, and the desired deprotected compound was eluted with 5–10% methanol in dichliromethane. Appropriate fractions were combined, solvents removed by evaporation, and the residue was dried by coevaporation with dry pyridine. The oily residue was redissolved in dry pyridine, dimethoxytritylchloride (1.2 eq) was added and the reaction mixture was left under anhydrous conditions overnight. The reaction was quenched with methanol (20 ml), evaporated, dissolved in chloroform, washed with saturated aq sodium bicarbonate and brine. Organic layer was dried over sodium sulfate and evaporated. The residue was purified by flash chromatography on silica gel to give 5'-O-Dimethoxytrityl derivatives with 70–80% yield.

Method B. Alternatively, 5'-O-Dimethoxytrityl-2'O-Methylthiomethyl-Nucleosides (6) may also be synthesized using 5'-O-Dimethoxytrityl-3'-O-t-Butyl-dimethy-Isilyl Nucleosides (4) as the starting material. Compound 4 is commercially available as a by-product during RNA phosphoramidite synthesis. Compond 4 is converted in to 3'-O-t-butyldimethylsilyl-2'-O-methylthiomethyl nucleoside 5, as described under example 3. The solution of the base-protected 3'-O-t-butyldimethylsilyl-2'-O-methylthiomethyl nucleoside 5 (2.00 mmol) in 10 ml of dry tetrahydrofuran (THF) was treated with 1M solution of tetrabutylammoniumfluoride in THF (3.0 ml) for 10–15 minutes at room temperature. The resulting mixture was evaporated, and purified by flash silica gel chromatography to give nucleosides 6 in 90% yield.

Example 5: 5'-O-Dimethoxytrityl-2'-O-Methylthiomethyl-Nucleosides-3'-(2-Cyanoethyl-N,N-diisopropylphosphoroamidites) (7)

Standard phosphitylation of nucleoside 6 according to Scaringe, S. A.; Franklyn, C.; Usman, N. *Nucleic Acids Res.* 1990, 18, 5433–5441 yielded phosphoramidites in 70–85% yield.

Example 6: General procedure for the synthesis of 2'-O-Methylthiophenyl nucleosides.

To a stirred ice-cooled solution of the mixture of base-protected 3',5'-O-(tetraisopropyldisiloxane-1,3-diyl) nucleoside (14,7 mmol) , thioanisole (147 mmol), N,N- dimethylaminopyridine (58.8 mmol) in acetonitrile (100 mL) under positive pressure of argon, benzoyl peroxide (36.75 mmol) was added portionwise over 3 hours. After complete addition the reaction mixture was allowed to warm to room temperature and was stirred under argon for an additional 1 hour. The solvents were removed in vacuo, the residue was dissolved in ethylacetate, washed twice with saturated aq NaHCO$_3$ and brine. The organic layer was dried over sodium sulfate and evaporated to dryness. The residue was purified by flash chromatography on silica using mixture EtOAc-hexanes (1:1) as eluent to give the corresponding methylthiophenyl nucleosides with 55–65% yield.

Example 7: 5'-O-Dimethoxytrityl-2'-O-Methylthiophenyl-Nucleosides.

These compounds were prepared as described above under examples 3 and 4.

Example 8: 5'-O-Dimethoxytrityl-2'-O-Methylthiophenyl-Nucleosides-3'-(2-Cyanoethyl N,N-diisopropylphosphoroamidites)

Standard phosphitylation according to Scaringe, S. A.; Franklyn, C.; Usman, N. *Nucleic Acids Res.* 1990, 18, 5433–5441 yielded phosphoramidites in 70–85% yield.

Example 9: Ribozymes containing 2'-O-methylthiomethyl substitutions

In a non-limiting example 2'-O-methylthioalkyl substitutions were made at various positions within a hammerhead ribozyme motif (FIG. 7, including U4 and U7 positions). Stromelysin mRNA site 617 was used as the target site for hammerhead ribozyme in this non-limiting example.

Hammerhead ribozymes (see FIG. 7) were synthesized using solid-phase synthesis, as described above. Several positions were modified, individually or in combination, with 2'-O-methylthiomethyl groups.

RNA cleavage assay in vitro:

Substrate RNA is 5' end-labeled using [γ-$^{32}$P] ATP and T4 polynucleotide kinase (US Biochemicals). Cleavage reactions were carried out under ribozyme "excess" conditions. Trace amount ($\leq 1$ nM) of 5' end-labeled substrate and 40 nM unlabeled ribozyme are denatured and renatured separately by heating to 90° C. for 2 min and snap-cooling on ice for 10–15 min. The ribozyme and substrate are incubated, separately, at 37° C. for 10 min in a buffer containing 50 mM Tris-HCl and 10 mM MgCl$_2$. The reaction is initiated by mixing the ribozyme and substrate solutions and incubating at 37° C. Aliquots of 5 μl are taken at regular intervals of time and the reaction is quenched by mixing with equal volume of 2× formamide stop mix. The samples are resolved on 20% denaturing polyacrylamide gels. The results are quantified and percentage of target RNA cleaved is plotted as a function of time.

Referring to FIG. 8, hammerhead ribozymes containing 2'-O-methylthiomethyl modifications at various positions cleave the target RNA efficiently. Surprisingly, all the 2'-O-methylthiomethyl -substituted ribozymes cleaved the target RNA more efficiently compared to the control hammerhead ribozyme.

Sequences listed in FIG. 7 and the modifications described in FIGS. 7 and 8 are meant to be non-limiting examples. Those skilled in the art will recognize that variants (base-substitutions, deletions, insertions, mutations, chemical modifications) of the ribozyme and RNA containing other combinations of 2'-hydroxyl group modifications can be readily generated using techniques known in the art, and are within the scope of the present invention.

Uses

The 2'-O-R$_3$-thio-R$_3$ and/or 2'-C-R$_3$-thio-R$_3$, wherein R$_3$ is independently a compound selected from a group consisting of alkyl, alkenyl, alkynyl, aryl, alkylaryl, carbocyclic aryl, heterocyclic aryl, amide and ester substituted nucleotides and/or non-nucleotides of this invention can be used to form stable oligonucleotides with enhanced activity as discussed above for use in enzymatic cleavage or antisense situations. Such oligonucleotides can be formed enzymatically using triphosphate forms by standard procedure. Administration of such oligonucleotides is by standard methods. See Sullivan et al., PCT WO 94/ 02595.

Diagnostic uses

Ribozymes of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be, determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides.

Requires a U in the target sequence immediately 5' of the cleavage site.

Binds 4–6 nucleotides at 5' side of cleavage site.

Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.

RNA portion of a ribonucleoprotein enzyme. Cleaves tRNA precursors to form mature tRNA.

Roughly 10 known members of this group all are bacterial in origin.

Hammerhead Ribozyme

Size: ~13 to 40 nucleotides.

Requires the target sequence UH immediately 5' of the cleavage site.

Binds a variable number nucleotides on both sides of the cleavage site.

14 known members of this class. Found in a number of plant pathogens (virusoids) that use RNA as the infectious agent (FIGS. 1 and 2)

Hairpin Ribozyme

Size: ~50 nucleotides.

Requires the target sequence GUC immediately 3' of the cleavage site.

Binds 4–6 nucleotides at 5' side of the cleavage site and a variable number to the 3' side of the cleavage site.

Figure 3:
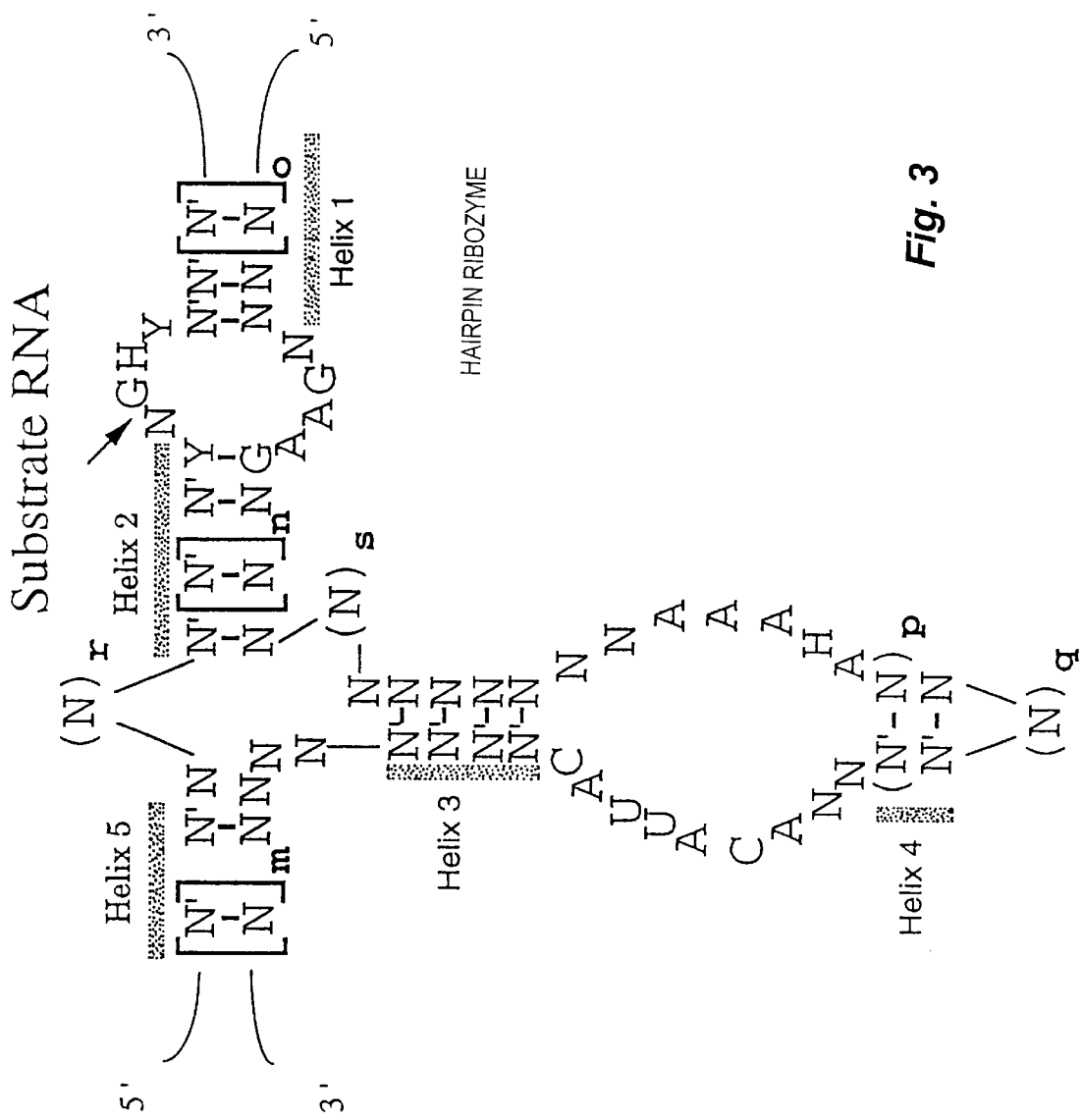

Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Size: 50–60 nucleotides.

Cleavage of target RNAs recently demonstrated.

Sequence requirements not fully determined.

Binding sites and structural requirements not fully determined, although no sequences 5' of cleavage site are required.

Figure 4:
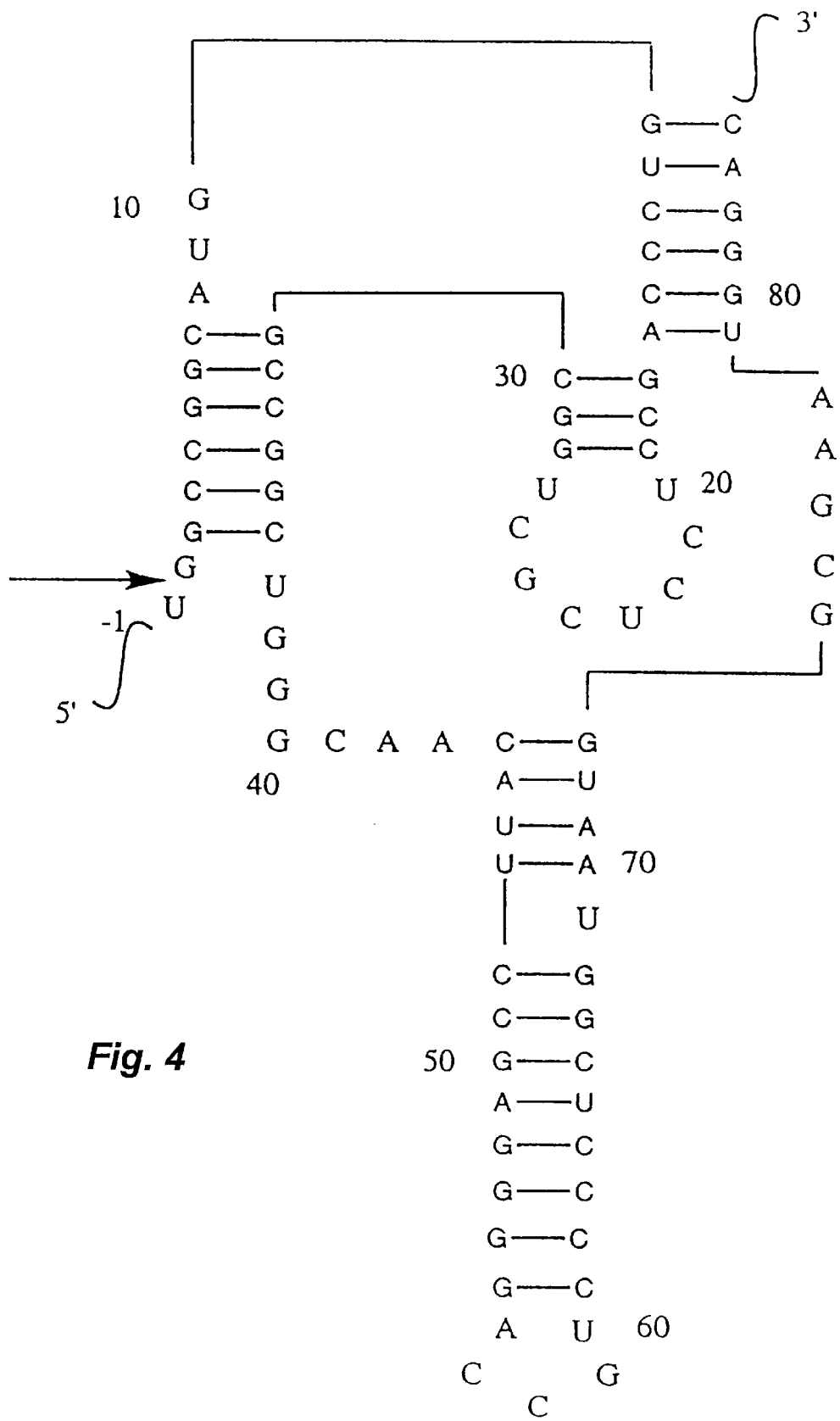
FIG. 4 (SEQ ID NO: 5) is a representation of the general structure of the hepatitis delta virus ribozyme domain known in the art.

Only 1 known member of this class. Found in human HDV (FIG. 4).

Neurospora VS RNA Ribozyme

Size: ~144 nucleotides

Cleavage of target RNAs recently demonstrated.

Sequence requirements not fully determined.

Figure 5:
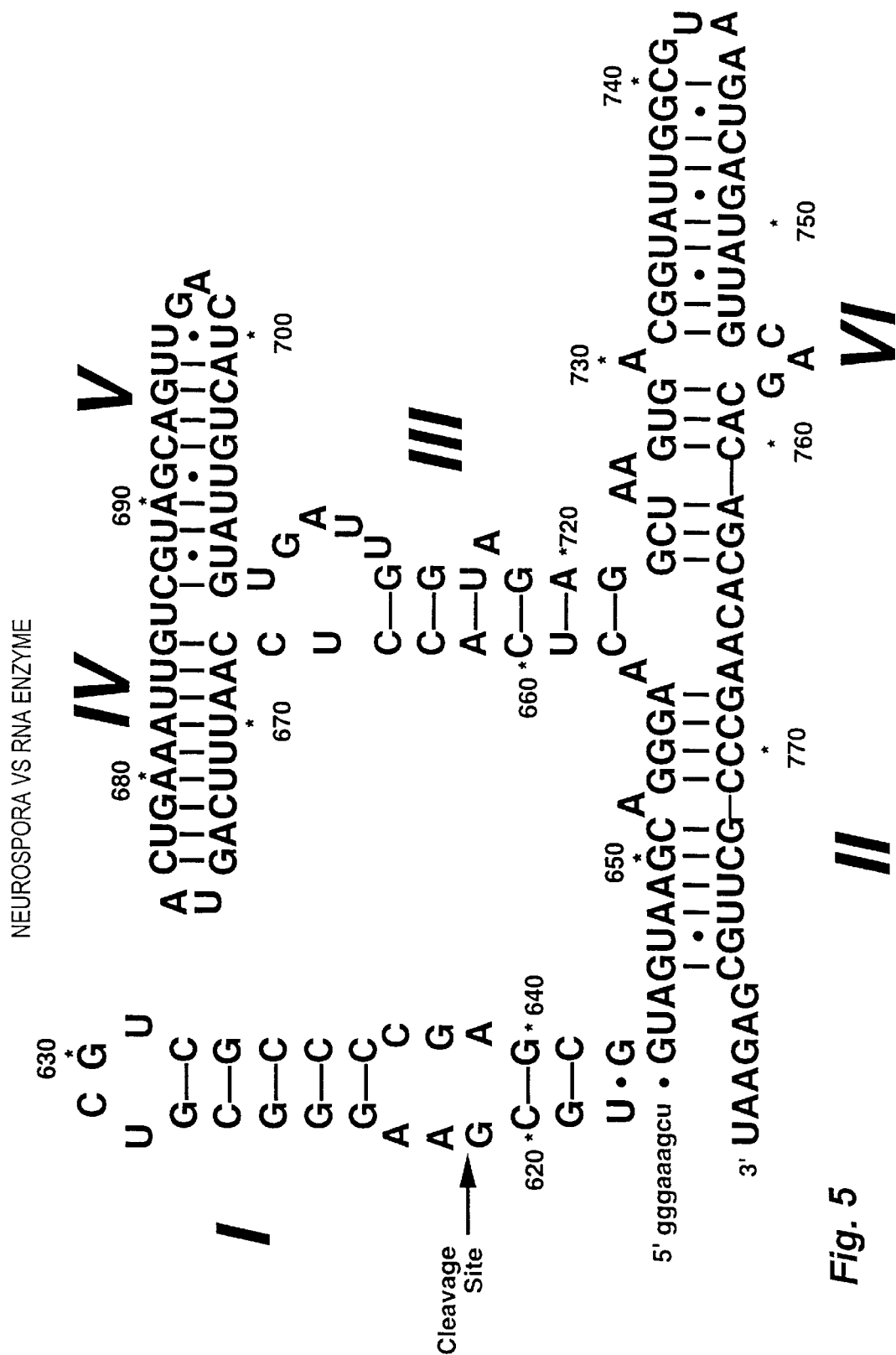
FIG. 5 (SEQ ID NO: 6) is a representation of the general structure of the self-cleaving VS RNA ribozyme domain.

Binding sites and structural requirements not fully determined. Only 1 known member of this class. Found in Neurospora VS RNA (FIG. 5).

---

We claim:

1. A method for producing an enzymatic nucleic acid molecule having activity to cleave an RNA or a single-stranded DNA molecule, wherein said enzymatic nucleic acid molecule comprises a modified nucleotide, wherein said modified nucleotide has the formula:

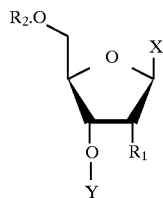

wherein, R1 is independently 2'-O-$R_3$-thio-$R_3$ or 2'-C-$R_3$-thio-$R_3$, wherein said $R_3$ is independently a compound selected from a group consisting of alkyl, allyl, alkenyl, alkynyl, aryl, alkylaryl, carbocyclic aryl, heterocyclic aryl, amide and ester; X is independently a base or H; Y is independently a phosphorus-containing group; and $R_2$ is independently a phosphorus-containing group;

comprising the step of incorporating said modified nucleotide into said enzymatic nucleic acid molecule.

2. The method of claim 1, wherein the step of incorporation of the modified nucleotide into said enzymatic nucleic acid molecule is by solid phase synthesis.

3. The method of claim 1, wherein the step of incorporation of the modified nucleotide into said enzymatic nucleic acid molecule is by using an enzyme.

4. The method of claim 1, wherein said enzymatic nucleic acid molecule is in a hammerhead motif.

5. The method of claim 1, wherein said enzymatic nucleic acid molecule is in a hairpin motif.

6. The method of claim 1, wherein said modified nucleotide is a 2'-O-methylthiomethyl nucleotide.

* * * * *